(12) United States Patent
Kizaki et al.

(10) Patent No.: US 8,921,616 B2
(45) Date of Patent: Dec. 30, 2014

(54) METHOD FOR PRODUCING GLYCOL FROM POLYHYDRIC ALCOHOL

(75) Inventors: Tetsuro Kizaki, Ichihara (JP); Keizo Iwatani, Ichihara (JP); Xin Chen, Toyama (JP); Satoshi Sato, Chiba (JP)

(73) Assignees: Clariant Catalysts (Japan) K.K., Tokyo (JP); National University Corporation Chiba University, Chiba (JP)

( * ) Notice: Subject to any disclaimer, the term of this patent is extended or adjusted under 35 U.S.C. 154(b) by 0 days.

(21) Appl. No.: 13/979,373

(22) PCT Filed: Jan. 12, 2012

(86) PCT No.: PCT/JP2012/050419
§ 371 (c)(1),
(2), (4) Date: Jul. 11, 2013

(87) PCT Pub. No.: WO2012/096323
PCT Pub. Date: Jul. 19, 2012

(65) Prior Publication Data
US 2013/0338405 A1 Dec. 19, 2013

(30) Foreign Application Priority Data
Jan. 13, 2011 (JP) ................................ 2011-004734

(51) Int. Cl.
C07C 27/04 (2006.01)
C07C 27/00 (2006.01)
C07C 29/145 (2006.01)
B01J 23/50 (2006.01)
B01J 23/89 (2006.01)
C07C 29/143 (2006.01)
C07C 45/52 (2006.01)

(52) U.S. Cl.
CPC .............. *C07C 29/145* (2013.01); *B01J 23/50* (2013.01); *B01J 23/8926* (2013.01); *B01J 23/8993* (2013.01); *C07C 29/143* (2013.01); *C07C 45/52* (2013.01)
USPC .......................................... 568/862; 568/861

(58) Field of Classification Search
None
See application file for complete search history.

(56) References Cited

U.S. PATENT DOCUMENTS

| | | | | |
|---|---|---|---|---|
| 3,360,567 A | * | 12/1967 | Johnson | 568/405 |
| 5,426,249 A | | 6/1995 | Haas et al. | |
| 2009/0088317 A1 | * | 4/2009 | Frye et al. | 502/178 |

FOREIGN PATENT DOCUMENTS

| | | | |
|---|---|---|---|
| JP | H05-255157 | | 10/1993 |
| JP | 2007-283175 | | 11/2007 |
| JP | 2009-298734 | | 12/2009 |
| WO | 2007053705 | | 5/2007 |
| WO | 2010150278 | * | 12/2010 |

OTHER PUBLICATIONS

Zhou et al., Green Chemistry, 2010, vol. 12, pp. 1835-1843.*
Zhou et al., "Selective hydrogenolysis of glycerol to propanediols on supported Cu-containing bimetallic catalysts", Green Chemistry, Oct. 2010, pp. 1835-1843, vol. 12, No. 10.
Dasari et al., "Low-pressure hydrogenolysis of glycerol to propylene glycol", Applied Catalysis A, Jan. 1, 2005, pp. 225-231, vol. 281.
Huang et al., "Continuous production of 1,2-propanediol by the selective hydrogenolysis of solvent-free glycerol under mild conditions", Journal of Chemical Technology and Biotechnology, Jun. 9, 2008, pp. 1670-1675, vol. 83, No. 12.
Akiyama et al., "Dehydration-hydrogenation of glycerol into 1,2-propanediol at ambient hydrogen pressure", Applied Catalysis A, Sep. 22, 2009, pp. 60-66, vol. 371, No. 1-2.
"Written Opinion of the International Search Authority (PCT/ISA/237)", mailed on Mar. 27, 2012, pp. 1-5.
"1st Office Action of China Counterpart Application", with English translation thereof, issued on Apr. 29, 2014, p. 1-p. 9.

* cited by examiner

*Primary Examiner* — Karl J Puttlitz
(74) *Attorney, Agent, or Firm* — Jianq Chyun IP Office

(57) ABSTRACT

An object of the invention is to provide a production method that can produce glycol from polyhydric alcohol with high selectivity and in a satisfactory yield. The object is achieved by using a silver catalyst in a reaction for synthesizing hydroxyketone from polyhydric alcohol having adjacent hydroxyl groups, and a hydrogenation catalyst in a reaction for synthesizing glycol from hydroxyketone.

5 Claims, No Drawings

US 8,921,616 B2

METHOD FOR PRODUCING GLYCOL FROM POLYHYDRIC ALCOHOL

CROSS-REFERENCE TO RELATED APPLICATION

This application is a 371 of international application of PCT application serial no. PCT/JP2012/050419, filed on Jan. 12, 2012, which claims the priority benefit of Japan application no. 2011-004734, filed on Jan. 13, 2011. The entirety of each of the above-mentioned patent applications is hereby incorporated by reference herein and made a part of this specification.

TECHNICAL FIELD

The present invention relates to a method for producing glycols such as propylene glycol from polyhydric alcohol such as glycerol efficiently and in a high yield.

BACKGROUND ART

Glycols typified by propylene glycol are used as a polyester raw material, an organic solvent, a reaction intermediate or the like, and are an important substance on a chemical industry.

Propylene glycol has been synthesized by hydrating propylene oxide so far.

Propylene being a raw material of propylene oxide is a fossil-resources-derived compound prepared by using naphtha as a main component. From a viewpoint of tackling recent environmental problems such as global warming, a development of a method for producing propylene glycol without using the raw material derived from the fossil resources has been desired.

In such a situation, a method for producing glycol from hydroxyketone without using propylene as a raw material (see Patent literature No. 1), or a method for producing glycol from polyhydric alcohol through hydroxyketone (see Patent literature No. 2) have recently been proposed. In the methods, a multi-step reaction is applied and a yield is insufficient. Thus, the method has left room for improvement in view of efficiency.

On the one hand, methods for directly producing propylene glycol from glycerol under hydrogen coexistence have already been reported (see Non-patent literature Nos. 1 to 4, Patent literature Nos. 3 to 5). In these methods, propylene glycol is considered to be directly formed by using a copper catalyst having both catalytic ability of a dehydration reaction for converting glycerol into hydroxyacetone and catalytic ability for hydrogenating the formed hydroxyacetone, or the like to allow a two-step reaction to progress in one reaction system. However, selectivity and a yield of propylene glycol obtained are not sufficient. In particular, conversion is low in a liquid-phase reaction, and the methods have been inefficient (see Non-patent literature No. 2). Moreover, reaction pressure is high, and the methods have had a problem of pressure resistance required for a reaction apparatus. On the other hand, a method for carrying out a reaction under atmospheric pressure has been also disclosed, but under a current situation, selectivity and a yield of propylene glycol are not sufficient in a similar manner (see Non-patent literature No. 3), or a large excess of hydrogen is required (see Non-patent literature No. 4).

CITATION LIST

Patent Literature

Patent literature No. 1: JP H5-255157 A.
Patent literature No. 2: U.S. Pat. No. 5,426,249 B.
Patent literature No. 3: WO 2007/053705 A.
Patent literature No. 4: JP 2007-283175 A.
Patent literature No. 5: JP 2009-298734 A.

Non-Patent Literature

Non-patent literature No. 1: Applied Catalysis A 281 2005 225-231.
Non-patent literature No. 2: Green Chemistry 2010, DOI: 10. 1039/c0gc00058b.
Non-patent literature No. 3: Journal of Chemical Technology and Biotechnology 2008, DOI: 10. 1002/jctb.
Non-patent literature No. 4: Applied Catalysis A 371 2009 60-66.

SUMMARY OF INVENTION

Technical Problem

In the methods, proposed in Patent literature No. 3 or 4 above, for synthesizing glycol by using a catalyst such as copper having both catalytic ability of a dehydration reaction and hydrogenation ability, glycol can be directly synthesized from polyhydric alcohol. However, a by-product is easily formed in the dehydration reaction for conversion from polyhydric alcohol into hydroxyketone, and as a result, the methods have a problem of a decreased yield of glycol being a final product.

More specifically, an object of the invention is to solve a conventional technical problem described above, and is to provide a method for producing glycol from polyhydric alcohol with high selectivity and in a satisfactory yield.

Solution to Problem

The inventors have diligently continued to conduct research, and as a result, have found that, when a silver catalyst is used, hydroxyketone being an intermediate of glycol synthesis can be synthesized from polyhydric alcohol with a high rate of reaction and with high selectivity. Meanwhile, it has been found that the hydrogenation ability of the silver catalyst was poor and thus the formed hydroxyketone cannot be sufficiently converted into glycol. The inventors have found that glycol can be produced in a satisfactory yield in combination with a reaction for synthesizing glycol from hydroxyketone by using a hydrogenation catalyst. Furthermore, the inventors have found that, when the silver catalyst and the hydrogenation catalyst are allowed to coexist, a two-step reaction to obtain glycol can be continuously progressed in one reaction system and in a satisfactory yield, and thus have achieved the invention.

A method for producing glycol according to the invention is as described below.

Item 1. A method for producing glycol from polyhydric alcohol having adjacent hydroxyl groups, comprising a reaction for synthesizing hydroxyketone from polyhydric alcohol by using a silver catalyst and a reaction for synthesizing glycol from the hydroxyketone formed in the reaction described above by using a hydrogenation catalyst.

Item 2. The method for producing glycol according to item 1, wherein the silver catalyst in the reaction for synthesizing hydroxyketone is supported on and/or compounded with a catalyst support including at least any one selected from the group consisting of aluminum oxide, silicon oxide, chromium oxide, cerium oxide, titanium oxide and zirconium oxide.

Item 3. The method for producing glycol according to item 1 or 2, wherein the hydrogenation catalyst in the reaction for synthesizing glycol contains at least any one selected from the group consisting of copper, cobalt, nickel, ruthenium, palladium, rhodium and platinum.

Item 4. The method for producing glycol according to any one of items 1 to 3, wherein the reaction for synthesizing hydroxyketone, and the reaction for synthesizing glycol continuously progress in one reaction system.

Item 5. The method for producing glycol according to item 4, wherein the reaction for synthesizing hydroxyketone, and the reaction for synthesizing glycol continuously progress in one reaction system by coexistence of the silver catalyst in the reaction for synthesizing hydroxyketone and the hydrogenation catalyst in the reaction for synthesizing glycol in one reaction system.

Item 6. The method for producing glycol according to item 4 or 5, using a catalyst containing both silver and copper.

Item 7. The method for producing glycol according to any one of items 1 to 6, wherein the polyhydric alcohol is glycerol and the glycol is propylene glycol.

Item 8. The method for producing glycol according to any one of items 1 to 7, wherein both the reaction for synthesizing hydroxyketone, and the reaction for synthesizing glycol are carried out at 280° C. or lower.

Item 9. The method for producing glycol according to any one of items 1 to 8, wherein both the reaction for synthesizing hydroxyketone, and the reaction for synthesizing glycol are carried out in a gas phase.

Advantageous Effects of Invention

According to the invention, glycol can be produced from polyhydric alcohol having adjacent hydroxyl groups efficiently and in a satisfactory yield. Moreover, when a silver catalyst and a hydrogenation catalyst are allowed to coexist, glycol can be synthesized from polyhydric alcohol continuously in one reaction system.

DESCRIPTION OF EMBODIMENTS

Reaction Mechanism in a Production Method According to the Invention

A production method according to the invention is characterized by including a reaction step (polyhydric alcohol dehydration reaction step) for synthesizing hydroxyketone from polyhydric alcohol having adjacent hydroxyl groups, and a reaction step (hydroxyketone hydrogenation reaction step) for synthesizing glycol from hydroxyketone synthesized.

In the reaction for synthesizing hydroxyketone from polyhydric alcohol, the adjacent hydroxyl groups in polyhydric alcohol cause a dehydration reaction to form a C=O group (carbonyl group), and in the reaction for synthesizing glycol from hydroxyketone, the formed C=O group (carbonyl group) of hydroxyketone is reduced into a C—OH group (hydroxyl group) by hydrogen, and thus glycol is formed.

An overall mechanism is a reaction in which one hydroxyl group in polyhydric alcohol is replaced by hydrogen.

(Raw Materials Used for the Production Method According to the Invention)

Specific examples of polyhydric alcohol having adjacent hydroxyl groups include trihydric or higher-hydric alcohol, in particular, glycerol and 1,2,3-butanetriol. When glycerol is used as a raw material, propylene glycol is formed, and when 1,2,3-butanetriol is used as the raw material, 2,3-butanediol or 1,2-butanediol is formed.

The polyhydric alcohol may contain moisture. When moisture is contained, content thereof is not particularly limited, but is ordinarily more than 0% by weight to 98% by weight or less, preferably, in the range of 20% by weight or more to 80% by weight or less. When moisture is contained, moisture is adjusted in the range described above, and thus glycol can be synthesized with high selectivity.

(Reaction for Synthesizing Hydroxyketone from Polyhydric Alcohol)

The production method according to the invention is characterized by using a silver catalyst in the reaction for synthesizing hydroxyketone from polyhydric alcohol having adjacent hydroxyl groups. As a typical catalyst used upon synthesizing glycol from polyhydric alcohol, copper is known. However, the inventors have obtained a finding in which, when the copper catalyst is used, a by-product other than hydroxyketone is easily formed, and as a result, a decrease in a yield of glycol being a final product is caused (see Non-patent literature No. 4).

Then, when the inventors have continued to conduct research, the inventors have found that, in the reaction for synthesizing hydroxyketone from polyhydric alcohol, use of silver as the catalyst allows synthesis of hydroxyketone in a more satisfactory yield in comparison with use of the copper catalyst.

(Catalyst in the Reaction for Synthesizing Hydroxyketone)

As the silver catalyst used in the reaction, a commercial item can be used directly or a product prepared by reducing the commercial item can also be used. Moreover, the silver catalyst of the invention may be supported on a catalyst support by a publicly known impregnation method or the like, or may be compounded therewith by a publicly known coprecipitation method or the like. The support on which the silver catalyst is supported or with which the silver catalyst is compounded is not particularly limited, if the support is ordinarily used as the catalyst support. Specific examples include supports containing aluminum oxide, silicon oxide, chromium oxide, cerium oxide, titanium oxide, zirconium oxide and silica alumina. In particular, in a case where silicon oxide is used as the support, a specific surface area is large, and hydroxyketone can be efficiently synthesized, and therefore such a case is preferred.

When the silver catalyst is prepared, a silver component only needs to be incorporated at a degree of developing a catalyst function, and content is ordinarily in the range of 0.01% by weight or more to 50% by weight or less, preferably, 0.5% by weight or more to 20% by weight or less. When the content is in the range described above, a silver catalyst performance can be sufficiently obtained.

(Reaction for Synthesizing Glycol from Hydroxyketone)

The production method according to the invention needs the reaction separately using the hydrogenation catalyst for synthesizing glycol being a final object from synthesized hydroxyketone. When a catalyst such as copper having both dehydration catalyst ability and hydrogenation ability is used, glycol is directly obtained from polyhydric alcohol, and therefore no separate reaction is needed. However, the silver catalyst being a feature of the invention has a poor hydrogenation ability, and is quite difficult to synthesize glycol from hydroxyketone in a satisfactory yield.

Therefore, the inventors have decided to arrange the reaction for synthesizing glycol from hydroxyketone by using the hydrogenation catalyst. The inventors have found that, when the reaction for synthesizing hydroxyketone from polyhydric alcohol by using the silver catalyst and the reaction=for synthesizing glycol from hydroxyketone by using the hydrogenation catalyst are combined, glycol can be finally synthesized efficiently.

(Catalyst in the Reaction for Synthesizing Glycol)

As the catalyst in the reaction for synthesizing glycol from hydroxyketone, any catalyst can be used, if the catalyst has hydrogenation ability. For example, copper, cobalt, nickel and a platinum group element such as ruthenium, palladium, rhodium and platinum are particularly preferred because such a catalyst has a high activity. As the catalysts, such a product can be used as a commercial item, a product prepared by reducing the commercial item, a product prepared by precipitating metal oxide from a commercially available metal salt, calcinating the precipitate and performing reduction, or a product prepared from a commercially available metal salt by a publicly known method such as impregnation and coprecipitation.

Moreover, with respect to the hydrogenation catalyst, a surface area of the catalyst is preferably increased as a compounded product.

When the hydrogenation catalyst is prepared, a metal only needs to be incorporated at a degree of sufficiently developing a hydrogenation function, and content is ordinarily in the range of 1% by weight or more to 90% by weight or less, preferably, 20% by weight or more to 80% by weight or less. When the content is in the range described above, a sufficient catalyst activity power can be obtained.

(Production Method in which Two Reactions Continuously Progress in One Reaction System)

The inventors have found that, when the silver catalyst and the hydrogenation catalyst are allowed to coexist in one reaction system, the reaction for synthesizing hydroxyketone from polyhydric alcohol and the reaction for synthesizing glycol from hydroxyketone continuously progress, and glycol is directly obtained from polyhydric alcohol, and thus have arrived at the invention.

(Coexistence of the Silver Catalyst and the Hydrogenation Catalyst)

A method for allowing the silver catalyst and the hydrogenation catalyst to coexist in one reaction system is not particularly limited. A specific example includes an art for supporting both silver and a hydrogenation catalyst component onto a catalyst support having a large specific surface area. Specific examples of methods for preparing the catalyst include a method for supporting a hydrogenation catalyst component onto a silver catalyst, a method for supporting silver onto a hydrogenation catalyst, a method for simultaneously impregnating a soluble salt (e.g. copper nitrate) of a hydrogenation catalyst component metal and a soluble silver salt (e.g. silver nitrate) into a catalyst support to obtain the catalyst, and a method for obtaining the catalyst by a publicly known method of coprecipitating a soluble salt (e.g. copper nitrate) of a hydrogenation catalyst component metal and a soluble silver salt (e.g. silver nitrate).

As the catalyst containing both the silver catalyst and the hydrogenation catalyst, a catalyst containing both silver and copper (hereinafter, referred to as a silver-copper catalyst) is particularly preferred because the catalyst has a high activity.

When the silver catalyst and the hydrogenation catalyst are allowed to coexist in one catalyst, a weight ratio in content of the silver catalyst to the metal being a component of the hydrogenation catalyst only needs to be incorporated at a degree of developing functions of both the catalysts, and the weight ratio is ordinarily in the range of 1:1,000 to 1:5, preferably, in the range of 1:500 to 1:50, further preferably, in the range of 1:200 to 1:25. If the weight ratio is adjusted in the range described above, glycol can be efficiently synthesized from polyhydric alcohol.

(Reaction Conditions in Each Reaction)

A reaction apparatus used in the method for producing glycol according to the invention is not particularly limited. Industrially, a gas-phase flow reaction apparatus of a type in which a raw material is gasified to pass the gas through a suitable catalyst layer and to allow the reaction is preferred. When the gas-phase flow reaction apparatus is used, for example, a predetermined catalyst is put into a reaction system in the gas-phase flow reaction apparatus, and the catalyst is pretreated by a publicly known method, and thus an active catalyst layer can be formed in the reaction system in the apparatus. Moreover, the gas-phase flow reaction apparatus may have one or a plurality of the reaction systems. For example, when the reaction for synthesizing hydroxyketone from polyhydric alcohol and the reaction for synthesizing glycol from synthesized hydroxyketone are separated and allowed to progress in another reaction system, the silver catalyst is preferably arranged on a side upstream of a flow system. Polyhydric alcohol being the raw material is gasified and fed to allow progress of a target reaction in the reaction system, and thus glycol can be finally produced.

As the pretreatment of the catalyst, a publicly known method by which the catalyst layer can be activated can be applied. A specific method includes an art for activating the catalyst layer by applying heat treatment at 200° C. for about 30 minutes to about 1 hour in a hydrogen flow.

Pressure conditions in the reaction for synthesizing hydroxyketone from polyhydric alcohol and the reaction for synthesizing glycol from hydroxyketone according to the invention may be under atmospheric pressure or under pressure. "Atmospheric pressure" in the invention means about one atmospheric pressure (about 0.1 MPa) in absolute pressure, which is not strictly limited to a condition of only one atmospheric pressure, but includes a range that is appreciated as the range of atmospheric pressure by those skilled in the art in the invention. On the other hand, an expression "under pressure" means pressure higher than about one atmospheric pressure in absolute pressure, and an upper limit thereof is not particularly placed, but as a pressure range in which cost of a reaction apparatus is not increased, the pressure range is ordinarily 5 MPa or less, preferably, 2 MPa or less, further preferably, 1 MPa or less, significantly preferably, 0.6 MPa or less.

Moreover, a method for introducing hydrogen used for the reaction for synthesizing glycol from hydroxyketone is not particularly limited, but hydrogen is preferably introduced as a carrier gas or in coexistence with the other carrier gas. Moreover, hydrogen plays a role of keeping activity of the catalyst in the reaction for synthesizing hydroxyketone from polyhydric alcohol. In particular, when progress of two reactions is continuously allowed, it is preferred that the carrier gas in which hydrogen is contained is used because the reaction is efficient by the viewpoint described above. Inflow of the carrier gas is appropriately set up depending on a size of the reaction apparatus, liquid hourly space velocity per unit hour (LHSV; unit, $h^{-1}$) of the raw material based on a catalyst volume, or the like. A ratio of the carrier gas to the raw material is ordinarily 1:1 to 100, preferably, 1:5 to 50 in a molar ratio.

With regard to temperatures in the reaction for synthesizing hydroxyketone from polyhydric alcohol and the reaction for synthesizing glycol from hydroxyketone according to the invention, although the temperatures depend on the pressure conditions, the reactions are preferably carried out at a temperature in which polyhydric alcohol ordinarily exists in a gas-phase state. Specifically, the reactions are carried out ordinarily in the range of 180° C. or more to 280° C. or less, preferably, in the range of 200° C. or more to 240° C. or less. Moreover, when the pressure is high, polyhydric alcohol liquefies in the reaction apparatus, causing a decrease in reaction efficiency, and therefore setting of temperature and pressure is required in consideration of the fact.

With regard to an amount of the catalyst and reaction time for producing glycol to be applied in the invention, in a case of a gas-phase flow reaction, contact time represented by liquid hourly space velocity per unit time (LHSV, unit: $h^{-1}$) based on the catalyst volume can be applied in the range of 0.1 to 5.0 $h^{-1}$, and from a viewpoint of a catalyst life and a yield, preferably, in the range of 0.15 to 3.0 $h^{-1}$, further preferably, in the range of 0.2 to 2.0 $h^{-1}$ in terms of a LHSV value.

supported on commercially available silicon dioxide (CARiACT Q10, made by Fuji Silysia Chemical Ltd.), and then calcinating the catalyst precursor at 500° C. for 3 hours under an air atmosphere.

Then, 7.8 mL of the catalyst prepared as described above was arranged in a gas-phase reaction apparatus, and pretreatment was applied at 220° C. for 30 minutes by allowing a hydrogen gas to flow from above at a flow rate of 30 mL/min under atmospheric pressure. After the pretreatment, a hydroxyacetone synthetic reaction was carried out by increasing inflow of hydrogen to 700 mL/min, and feeding an 80 wt % glycerol aqueous solution to the catalyst layer at a LHSV of 0.25 $h^{-1}$. The results are represented in Table 1.

Comparative Example 1

A hydroxyacetone synthetic reaction was carried out in a manner similar to the operations in Reference Example except that copper was supported onto a support using copper nitrate (guaranteed reagent, made by Wako Pure Chemical Industries, Ltd.) in place of silver nitrate in catalyst preparation. The results are represented in Table 1.

TABLE 1

|  | Catalyst | Catalyst amount (mL) | LHSV ($h^{-1}$) | Reaction temperature (° C.) | Rate of reaction (%) | Hydroxyacetone selectivity (%) | Yield (%) |
| --- | --- | --- | --- | --- | --- | --- | --- |
| Reference Example | 10% Ag/SiO2-Q10 | 7.8 | 0.25 | 220 | 98.8 | 91.5 | 90.4 |
| Comparative Example 1 | 10% Cu/SiO2-Q10 | 7.8 | 0.25 | 220 | 99.8 | 30.9 | 30.8 |

EXAMPLES

Hereinafter, advantageous effects of the invention will be specifically explained by way of Examples, but the invention is in no way limited to the Examples.

In evaluation of performance in Examples, Comparative Examples and Reference Examples, as a reactor, an apparatus in which a 150 mm catalyst layer was arranged in a fixed bed pressurized gas-phase flow reaction apparatus having an internal diameter of 28 mm and an overall length of 1,000 mm was used. The reactor has in an upper end a carrier gas entry and a material inlet, and has in a lower end a crude reaction mixture collection container (cooled) from which a gas is discharged through a back pressure regulating valve. A crude reaction mixture collected in the collection container was measured by gas chromatography, measured values were corrected using a calibration curve, and then a remaining amount of raw material such as glycerol, and a yield of a product such as hydroxyacetone and propanediol were determined, and from the values, a rate of reaction (mol %), selectivity (mol %) and a yield (mol %) were determined.

Reference Example

Synthesis of Hydroxyacetone Using a Silver Catalyst

Catalytic activity of a silver catalyst in a reaction for synthesizing hydroxyketone from polyhydric alcohol (glycerol to hydroxyacetone) was evaluated.

The silver catalyst was obtained by preparing a catalyst precursor, according to an impregnation method using silver nitrate (guaranteed reagent, made by Wako Pure Chemical Industries, Ltd.), to be 10% by weight in an amount of silver The results in Table 1 clearly show that, when the silver catalyst is used (Reference Example) in the reaction for synthesizing hydroxyacetone from glycerol, hydroxyacetone can be synthesized with a higher rate of reaction and higher selectivity.

Examples 1, 2 and 3

Synthesis of Propylene Glycol Using a Silver-Copper Catalyst

Activity of a silver-copper catalyst in which a silver catalyst and a hydrogenation catalyst (copper catalyst) coexisted was evaluated in a production method for synthesizing propylene glycol (glycol) from glycerol (polyhydric alcohol).

As the silver-copper catalyst, a product prepared, according to an impregnation method, by supporting onto a copper chromium catalyst (T-4419, made by Sud-Chemie Catalysts Inc.) silver in an amount of addition described in Table 2 was used. Various kinds of reaction conditions, a rate of reaction, selectivity of hydroxyacetone, selectivity of propylene glycol, and a yield are represented in Table 2.

Comparative Example 2

As Comparative Example, a copper chromium catalyst (T-4419, made by Sud-Chemie Catalysts Inc.) in which no material is added was used, and an evaluation in a manner similar to the evaluation in Example 1 was performed. The results are represented in Table 2.

TABLE 2

|  | Amount of Ag addition (%) | Reaction pressure (MPa) | Hydrogen flow (L/min) | LHSV (h⁻¹) | H₂/glycerol molar ratio | Reaction temperature (°C.) | Rate of reaction (%) | Selectivity HA | Selectivity PG | PG yield (%) |
|---|---|---|---|---|---|---|---|---|---|---|
| Example 1 | 2.5 | 0.3 | 5.4 | 0.48 | 31 | 219 | 100 | 4.6 | 93.7 | 93.7 |
| Example 2 | 1.75 | 0.3 | 5.4 | 0.48 | 31 | 219 | 100 | 4.1 | 94.5 | 94.5 |
| Example 3 | 1.0 | 0.3 | 5.4 | 0.48 | 31 | 219 | 99.8 | 1.4 | 95.0 | 94.8 |
| Comparative Example 2 | 0.0 | 0.3 | 5.4 | 0.48 | 31 | 219 | 100 | 0.9 | 88.7 | 88.7 |

(HA, hydroxyacetone: PG, propylene glycol)

The results in Table 2 clearly show that, when the silver-copper catalyst was used (Examples 1, 2 and 3), propylene glycol can be synthesized in a more satisfactory yield in any amount of addition, in comparison with the copper catalyst only (Comparative Example 2). Moreover, Table 2 clearly shows that, while a ratio of forming a by-product other than hydroxyacetone and propylene glycol was higher in a case of the copper catalyst only, when the silver-copper catalyst was used, propylene glycol can be synthesized with a higher yield and a smaller amount of by-product.

Examples 4 to 10

Pressure Dependence in Synthesis of Propylene Glycol

The results of pressure dependence in synthesis of propylene glycol using a silver-copper catalyst are represented in Table 3.

TABLE 3

|  | Amount of Ag addition (%) | Reaction pressure (MPa) | Hydrogen flow (L/min) | LHSV (h⁻¹) | H₂/glycerol molar ratio | Reaction temperature (°C.) | Rate of reaction (%) | Selectivity HA | Selectivity PG | PG yield (%) |
|---|---|---|---|---|---|---|---|---|---|---|
| Example 4 | 1.0 | 0.2 | 5.4 | 0.48 | 31 | 219 | 99.6 | 3.2 | 93.8 | 93.4 |
| Example 5 | 1.0 | 0.4 | 5.4 | 0.48 | 31 | 219 | 100 | 1.2 | 95.5 | 95.5 |
| Example 6 | 1.0 | 0.5 | 5.4 | 0.48 | 31 | 219 | 100 | 1.3 | 96.1 | 96.1 |
| Example 7 | 1.0 | 0.6 | 5.4 | 0.48 | 31 | 219 | 100 | 0.8 | 96.5 | 96.5 |
| Example 8 | 1.75 | 0.4 | 5.4 | 0.48 | 31 | 218 | 100 | 1.7 | 96.2 | 96.2 |
| Example 9 | 1.75 | 0.5 | 5.4 | 0.48 | 31 | 218 | 100 | 1.3 | 96.8 | 96.8 |
| Example 10 | 1.75 | 0.6 | 5.4 | 0.48 | 31 | 218 | 100 | 1.1 | 97.1 | 97.1 |

(HA, hydroxyacetone: PG, propylene glycol)

Temperature Dependence in Synthesis of Propylene Glycol

Examples 11 to 13

The results of temperature dependence in synthesis of propylene glycol using a silver-copper catalyst are represented in Table 4.

TABLE 4

|  | Amount of Ag addition (%) | Reaction pressure (MPa) | Hydrogen flow (L/min) | LHSV (h⁻¹) | H₂/glycerol molar ratio | Reaction temperature (°C.) | Rate of reaction (%) | Selectivity HA | Selectivity PG | PG yield (%) |
|---|---|---|---|---|---|---|---|---|---|---|
| Example 11 | 1.75 | 0.4 | 5.4 | 0.48 | 31 | 214 | 100 | 2.3 | 96.1 | 96.1 |
| Example 12 | 1.75 | 0.4 | 5.4 | 0.48 | 31 | 222 | 100 | 1.1 | 96.1 | 96.1 |
| Example 13 | 1.75 | 0.4 | 5.4 | 0.48 | 31 | 228 | 99.8 | 2.6 | 94.0 | 93.8 |

(HA, hydroxyacetone: PG, propylene glycol)

The results in Tables 3 and 4 clearly show that, even in the case where the pressure and temperature conditions were close to liquefaction conditions of glycerol, namely, a high pressure and a low temperature, a yield of propylene glycol does not decrease, and the reaction further favorably progresses.

INDUSTRIAL APPLICABILITY

According to the invention, glycol can be produced from polyhydric alcohol having adjacent hydroxyl groups in a satisfactory yield and efficiently.

What is claimed is:

1. A method for producing glycol from polyhydric alcohol having adjacent hydroxyl groups, comprising a reaction for synthesizing hydroxyketone from polyhydric alcohol by using a silver catalyst and a reaction for synthesizing glycol from the hydroxyketone formed in the reaction described above by using a hydrogenation catalyst,
    wherein the reaction for synthesizing hydroxyketone and the reaction for synthesizing glycol continuously progress in one reaction system by using a catalyst containing both silver and copper and a gas-phase flow reaction apparatus, and pressure conditions in the reaction for synthesizing hydroxyketone and the reaction for synthesizing glycol are 1 MPa or less.

2. The method for producing glycol according to claim 1, wherein the catalyst containing both silver and copper is supported on and/or compounded with a catalyst support including at least any one selected from the group consisting of aluminum oxide, silicon oxide, chromium oxide, cerium oxide, titanium oxide and zirconium oxide.

3. The method for producing glycol according to claim 1, wherein the polyhydric alcohol is glycerol and the glycol is propylene glycol.

4. The method for producing glycol according to claim 1, wherein both the reaction for synthesizing hydroxyketone and the reaction for synthesizing glycol are carried out at 280° C. or lower.

5. The method for producing glycol according to claim 1, wherein both the reaction for synthesizing hydroxyketone and the reaction for synthesizing glycol are carried out in a gas phase.

\* \* \* \* \*